United States Patent [19]

Willoughby

[11] Patent Number: 4,830,319
[45] Date of Patent: May 16, 1989

[54] HOLDER FOR HYPODERMIC NEEDLE SHEATH

[76] Inventor: Graham M. Willoughby, 20 Ruskin Row, Winnipeg, Manitoba, Canada, R3M 2R7

[21] Appl. No.: 124,592

[22] Filed: Nov. 24, 1987

[30] Foreign Application Priority Data

Sep. 18, 1987 [CA] Canada ................................. 547224

[51] Int. Cl.[4] ............................................. F16M 11/00
[52] U.S. Cl. .................................. 248/176; 248/316.4
[58] Field of Search ................... 248/314, 309.1, 176, 248/316.1, 316.4; 211/69, 60.1, 13; 128/DIG. 6; 604/193, 192, 263; 294/515, 150; 269/157, 160; 81/3.4; 206/364, 365

[56] References Cited

U.S. PATENT DOCUMENTS

| | | | |
|---|---|---|---|
| 1,135,625 | 4/1915 | Savin | 211/69 X |
| 1,272,176 | 7/1918 | Alexander | 269/157 X |
| 1,566,483 | 12/1925 | Kraeer | 269/157 |
| 1,593,947 | 7/1926 | Miller et al. | 81/3.4 UX |
| 3,022,067 | 2/1962 | Stolz | 269/157 X |
| 4,430,082 | 2/1984 | Schwabacher . | |
| 4,559,042 | 12/1985 | Votel . | |
| 4,573,975 | 3/1986 | Frist | 604/263 X |
| 4,610,667 | 9/1986 | Pedicano et al. . | |
| 4,735,617 | 4/1988 | Nelson | 604/263 X |

OTHER PUBLICATIONS

"A Practical Program for Infection Control", Ash-/Dentsply, A Division of Dentsply International Inc. (1988).

*Primary Examiner*—J. Franklin Foss

[57] ABSTRACT

A holder for a sheath having an open end of the type used for the protection of hypodermic needles. The holder comprises a base adapted to resist tipping and sliding in use when supported on a surface, and a holder device associated with the base. The holding device is capable of temporarily holding the sheath with the open end outermost so that the sheath may be re-positioned over a hypodermic needle without risk of puncture by the needle of the user's hands. The holder avoids the risk to health field workers of becoming infected from a patient's bodily fluids by accidental puncturing of the user's hands when relocating the safety sheath on a hypodermic needle.

5 Claims, 2 Drawing Sheets

HOLDER FOR HYPODERMIC NEEDLE SHEATH

BACKGROUND OF THE INVENTION

1. FIELD OF THE INVENTION

This invention relates to devices used for providing safety and convenience for the users, such as doctors, dentists, nurses, patients, etc., of hypodermic syringes. More particularly, the invention relates to devices for reducing the risk of transmitting infections during the administration of hypodermic injections by health field workers and the like.

2. DISCUSSION OF THE PRIOR ART

One of the most common ways by which health field workers may contract infections from patients is by accidental exposure to a patient's bodily fluids during the administration of hypodermic injections. Hypodermic syringes are either of the disposable or re-usable type, but both types make use of needles which are protected by a narrow cap or sheath, i.e. a hollow tube open at one end and usually closed at the other with a collar at the open end for gripping the needle at the part which connects to the syringe. At the time an injection is given, the sheath is removed and is then replaced immediately following the injection. This procedure reduces the risk of accidental puncture by the needle except at the time when the sheath is being replaced on the needle. The average diameter of a sheath is about one quarter of an inch and slight misjudgement in replacing the sheath can result in a self-inflicted wound for the user.

There is accordingly a need for a device which reduces the risk of accidental punctures by hypodermic needles when the protective sheaths are being replaced on the needles after use.

SUMMARY OF THE INVENTION

An object of the invention is to provide a holder for temporarily holding a sheath while a hypodermic needle is being used and for enabling the sheath to be re-positioned on the needle without risk of accidental puncture by the needle.

The invention thus provides a holder of this kind which comprises a base and holding means for the sheath associated with the base. The base is adapted to resist tipping and sliding during use and the holding means is capable of temporarily holding a hypodermic sheath with the open end outermost, thereby permitting the sheath to be re-positioned on a needle without risk of accidental puncture.

The term "base" is intended to mean any kind of object or body capable of supporting, holding, defining or containing the sheath holding means. Further, the term "adapted to resist tipping and sliding during use" is intended to include bases that can be securely fixed to, or formed integrally with, a suitable support as well as bases that are freely supported by a suitable surface but are nevertheless difficult to tip or slide.

DETAILED DESCRIPTION OF THE PREFERRED EMBODIMENTS

Figure 1:
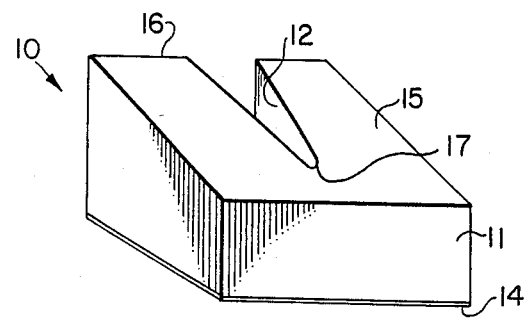
FIG. 1 is a perspective view of a holder, having a slot acting as the holding means, according to a first preferred embodiment of the invention.
Figure 2:
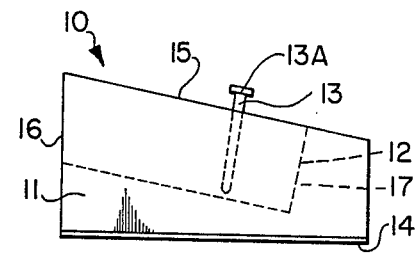
FIG. 2 is a side view of the holder of FIG. 1 with the slot shown in broken lines and a sheath shown in the slot.

A first preferred embodiment of the holder of the invention is shown in FIGS. 1 and 2.

The holder 10 comprises a base 11 having a longitudinal slot 12 which acts as holding means for a hypodermic sheath 13. The base is preferably quite heavy and this, coupled with its squat shape (i.e. its low vertical height and large supporting area) makes it difficult to tip over. The lower surface of the base preferably has a layer 14 of a slip-resistant material, such as a soft elastomeric polymer, so that the holder remains in place on a supporting surface, e.g. on a medical practitioner's tray.

The slot 12 extends into the base from the upper and rear surfaces 15 and 16, respectively. The slot is sufficiently deep to receive most or all of the length of the sheath 13 and tapers gradually inwardly towards the front end 17 so that it has a generally V-shaped outline when viewed from above.

The upper surface 15 slopes slightly downwardly towards the front of the base so that the position of the slot 12 can be readily seen, even by a user whose eye level is at the same general height as the upper surface 15, for example when the user is working in a sitting position.

The holder 10 is used as follows. The user first manually removes the sheath 13 from a hypodermic needle (not shown) and sets it in the slot 12 in the position shown in FIG. 2 with the open end 13A uppermost by moving the holder from the back towards the front of the slot until the tapering slot walls grip the sheath. Once the injection has been given, the user, holding the syringe by the barrel in one hand and keeping the other hand clear, inserts the needle into the sheath and pushed down until the sheath is firmly fixed on the needle. Since this can be done while the user's free hand (i.e. the one not holding the syringe) is kept well away from the sheath and needle, the risk of puncture is avoided. The sheath and needle can then be withdrawn from the holder by pushing the sheath with the syringe towards the back of the slot, preferably with a slight twisting or tilting motion to free the sheath. If the sheath is so firmly gripped by the slot walls that the base has to be firmly fixed in place to make removal possible, the user's free hand can be used to securely hold the base; but even when this is necessary, the hand need not be on or near the base when the needle is inserted into the sheath.

When multiple injections are to be given to the same patient, it is desirable to protect the user when the sheath is being removed from the needle as well as when the sheath is being replaced on the needle. In such cases, the sheath can be removed by holding the syringe by the barrel with the needle/sheath combination in the wide section of the slot 12, moving the syringe forwards until the needle/sheath combination is securely gripped by the slot walls and then pulling the syringe upwardly while twisting to remove the needle from the sheath.

The fact that the slot tapers in width from one end to the other means that sheaths of any width can be accommodated and that a firm gripping effect can be achieved.

If desired, the walls of the slot 12 may be roughened or coated with a suitable material to increase the frictional engagement between the sheath and the slot.

The holder is preferably made of a material, e.g. plastic or metal, particularly stainless steel, that can readily be sterilized by conventional means. If the holder is made of plastic, it may be weighted with metal either internally or externally in order to improve the resistance to tipping and slipping. Moreover, although the base 11 is shown as generally rectangular, it may have a more curved exterior to assist holding by the user's free hand.

For the ultimate in stability, the holder may of course be screwed, bolted, glued, clamped, etc. to a suitable supporting surface to resist tipping or sliding of the holder, in which case the weight and stability of the base itself when not secured to the support in this way is of lesser concern.

Figure 3:
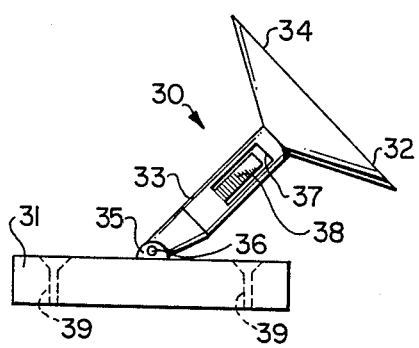
FIG. 3 is a side view of a holder according to a second preferred embodiment of the invention having tiltable holding means, with the holding means being tilted to a sloping position.
Figure 4:
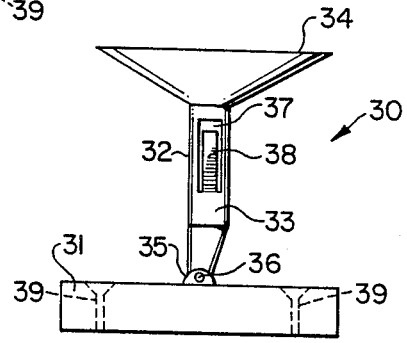
FIG. 4 is a view similar to FIG. 3 with the holding means being tilted to the upright position.

A second embodiment of the invention is shown in FIGS. 3 and 4. In this embodiment, the holder 30 comprises a base 31 and holding means 32 for a hypodermic sheath (not shown) mounted on the base.

The holding means comprises a hollow funnel-shaped body having a narrow cylindrical portion 33 adjacent to the base 31, and an outwardly widening conical section 34 at the free end of the body. The funnel-shaped body is attached to the base via a pivot 35 which allows the body to be tilted about a horizontal axis 36, but the moving surfaces of the pivot generate sufficient friction that the funnel-shaped body remains in any position to which it is moved.

The cylindrical portion 33 has an internal diameter that is wide enough to accommodate any sheath likely to be encountered and has an internal length sufficient to accept the entire sheath or a substantial part thereof.

In use, the user removes the sheath from a hypodermic needle by hand and places it, hole uppermost, in the cylindrical portion 33 of the funnel-shaped body. The conical upper section 32 assists this action because it guides the sheath to the cylindrical portion of the body. After the injection has been given, the user (holding the syringe by the barrel) inserts the used needle into the open end of the sheath located inside the holder, presses to secure the sheath on the needle and then removes the needle/sheath combination from the holder. This can normally be done without the user's free hand touching the holder. If the user wishes to steady the holder, however, the cylindrical section may be grasped with the user's free hand and risk of accidental puncture of the hand during the insertion of the needle into the sheath is eliminated by virtue of the conical section 34 which acts as a shield for the hand.

The pivotal attachment of the funnel-shaped body on the base permits the body to be tilted sideways as shown in FIG. 3 to permit easy insertion of the sheath into the holder, even when the user is working in a sitting position, but also permits the funnel-shaped body to be moved to the upright position of FIG. 4 so that the needle can be firmly pressed into the sheath without causing the holder to slide along a supporting surface.

When multiple injections are to be given, the holder can be used to remove the sheath as well as to hold it. For this purpose, the cylindrical section 33 has two inverted U-shaped slits 37 cut through the cylindrical wall at opposed locations. The slits define gripping tabs 38 which can be used to grip an inserted needle/sheath combination when the tabs are squeezed inwardly by the user's free hand. The tabs can grip the sheath securely so that the needle may be removed by twisting and pulling the syringe. The tabs can also be used to hold the sheath securely, if desired, when the needle is to be re-positioned in the sheath.

The base 31 is preferably made of a heavy material, such as metal (e.g. stainless steel), or a light material, such as plastic, suitably weighted with exterior or interior metal inserts. The funnel-shaped body is preferably made of metal or plastic and at least the conical section 34 should be puncture-resistant. The materials employed should preferably be sterilizable.

If desired, a non-slip layer such as the one used in the previous embodiment, may be provided on the underside of the base 31 or the base may be provided with holes 39 suitable for receiving screws or bolts, an adhesive layer or a clamp or the like for securely attaching the holder to a suitable support.

While the use of a conical section 34 is preferred, the same shielding effect for the user's free hand can of course be obtained by the substitution of an enlarged flat disc or plate t the upper end of the cylindrical section 32 or even by the provision of a downwardly and outwardly sloping conical section.

Figure 5:
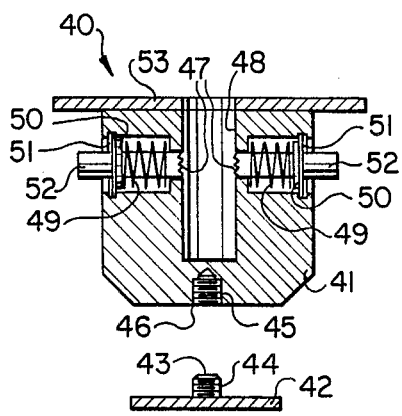
FIG. 5 is a cross-sectional partially exploded view of a holder according to a third preferred embodiment of the invention incorporating opposed means for gripping a needle sheath.

A further preferred holder 40 according to the invention is shown in FIG. 5. This holder comprises two parts, i.e. body 41 and a bracket 42. The bracket 42 is intended for permanent attachment (e.g. by means of an adhesive) to a supporting surface (not shown). A central upstanding pin 43 has an external screw thread 44 adapted to mate with an internal screw thread 45 in a central hole 46 in the underside of the body 41. By screwing the body 41 onto the bracket 42, the holder can be secured to a supporting surface but can readily be removed for cleaning and sterilization.

The holder 40 has opposed gripping elements 47 capable of extending horizontally through transverse parts into a central bore 48 forming the sheath holding means. The gripping elements are held in the retracted positions shown in the drawing by coil springs 49 which urge enlarged collars 50 on the gripping elements into engagement with retainer rings 51 fixed to the body 41. The extreme ends 52 of the gripping elements project through the retainer rings 51 and outwardly of the body 41.

In use, a needle and sheath combination attached to a hypodermic syringe can be located in the central bore 48 and the extreme ends 52 of the gripping elements pushed inwardly so that the needle and sheath combination is gripped between the inner ends of the gripping elements. The user can then twist and pull the syringe to remove the sheath, which then remains in the central bore. When the sheath is to be replaced on the needle, the process is reversed either with or without the operation of the gripping elements 47.

A plate 53 forming the top surface of the body 41 extends outwardly beyond the extreme ends 52 of the gripping elements in order to provide protection from puncture for the user's hand when operating the gripping elements.

Figure 6A:
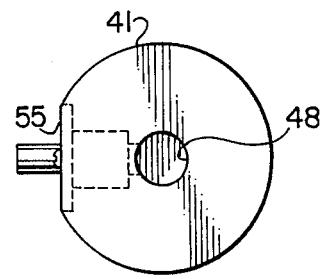
FIGS. 6A and 6B are a top plan view (with the top plate and gripping element removed) and a cross-sectional view, respectively, of a holder according to a fourth preferred embodiment of the invention incorporating single means for gripping a needle sheath.
Figure 6B:
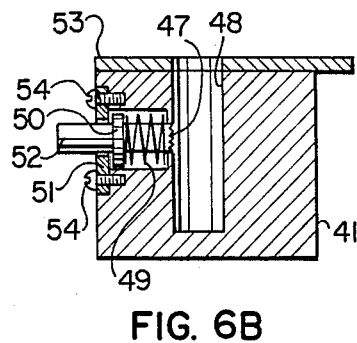

A similar embodiment is shown in FIGS. 6A and 6B (and similar parts have been identified by the same reference numerals), except that there is only one gripping element 47 in this case and there is no bracket 42 (the holder is intended just to be placed freely on a suitable supporting surface). Moreover, an external retainer ring 51 is held onto the body by means of screws 54. As shown in FIG. 6A (which is a top plan view with plate 53 and elements 47, 49, 51 and 54 removed), the body 41 is cylindrical except for a flat section 55 which accomodates the retainer ring 51.

Although only one gripping element 47 is provided, the sheath can be securely gripped because it becomes jammed between the gripping element and the opposite side of the central bore 48.

Figure 7A:
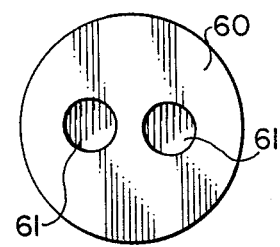
FIGS. 7A and 7B are a top plan view and a side elevational view of a holder according to a fifth preferred embodiment of the invention having multiple holding means of different longitudinal lengths.
Figure 7B:
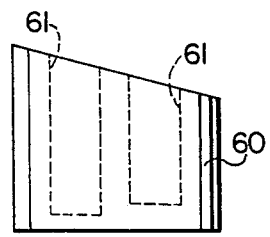

Yet another preferred holder is shown in FIGS. 7A and 7B. This comprises a base 60 and a pair of sheath holding means formed by bores 61. There are no gripping elements in this embodiment and a sheath is merely placed in one or other of the bores until it is required to re-cap the needle. The bores 61 are of different lengths in recognition of the fact that sheaths come in different lengths. Accordingly, a sheath can be placed in a bore 61 which most closely approximates its own length. Each bore 61 has a width greater than the maximum sheath width likely to be encountered.

While the embodiments described above are presently preferred, it will be apparent to persons skilled in this art that various alterations and modifications will be possible without departing from the scope of the invention as defined by the following claims. All such alterations and modifications form part of this invention.

I claim:

1. A holder for a safety sheath having an open end of the type used for the protection of a hypodermic needle, said holder comprising:
    a base adapted to resist tipping in use when supported on a surface and comprising a lower section having a size suitable to be firmly gripped by a user's hand, and an outwardly extending upper section for shielding said user's hand from needle punctures; and
    an elongated narrow hole extending downwardly into said base from an upper surface of said upper section, said hole forming holding means associated with said base for temporarily holding said sheath generally vertically with said open end outermost and for enabling said sheath to be re-positioned over a hypodermic needle without substantial risk of accidental puncture by said needle of said user's hand.

2. A holder according to claim 1 including at least one elongated gripping element longitudinally slidably mounted in a part in said base and having one end which may extend into said hole to grip a sheath located therein and an opposite end projecting outside said base.

3. A holder according to claim 2 wherein said at least one gripping element is biased by spring means to a retracted position in which said one end does not extend substantially into said hole.

4. A holder according to claim 2 wherein two elongated gripping elements are provided, the respective one ends of which are located in substantially diametrically opposed positions.

5. A holder according to claim 1 further comprising at least one additional elongated hole extending generally downwardly into said base from said upper surface, said holes being of different lengths to accommodate sheaths of different longitudinal sizes.

* * * * *